United States Patent [19]

Primes et al.

[11] Patent Number: 5,336,621
[45] Date of Patent: Aug. 9, 1994

[54] DIVALENT HAPTEN DERIVATIVES

[75] Inventors: Kathleen J. Primes; Gerald F. Sigler, both of San Diego, Calif.; Gerd Grenner; Wolfgang Kapmeyer, both of Marburg, Fed. Rep. of Germany

[73] Assignee: Hoechst Celanese Corporation, Somerville, N.J.

[21] Appl. No.: 211,940

[22] Filed: Jun. 27, 1988

Related U.S. Application Data

[60] Division of Ser. No. 69,747, Jul. 6, 1987, Pat. No. 4,760,142, which is a continuation-in-part of Ser. No. 825,425, Feb. 3, 1986, abandoned, which is a continuation-in-part of Ser. No. 675,374, Nov. 27, 1984, abandoned.

[51] Int. Cl.$^5$ ............................................. G01N 33/546
[52] U.S. Cl. ............................... 436/534; 436/500; 436/816
[58] Field of Search ............... 435/7; 436/524, 527, 436/532, 816, 822, 509, 534, 531, 518, 520, 815, 533, 500, 805; 530/388, 387, 380; 424/458, 469, 489

[56] References Cited

U.S. PATENT DOCUMENTS

| | | | |
|---|---|---|---|
| 4,341,758 | 7/1982 | Sakakibora et al. | 436/533 |
| 4,581,337 | 4/1986 | Frey et al. | 436/805 |
| 4,604,365 | 8/1986 | O'Neill et al. | 436/808 |

OTHER PUBLICATIONS

Pauling, L. et al. "Precip. Reactions of Antibodies & Polyhaptenic Substances." Journal Amer. Chem. Soc., vol. LXIV, 1942, pp. 2994–3003.

Nishikawa, T. et al. "Comp. Neph. Immuno. Method . . . ". Journal Immunological Methods, 29 (1979), pp. 85–89.

Green et al., "Detection of Antibody Monomers, Dimers, and Polymers upon interaction of A Homologous Series of Divalent Haptens w/its Specific Ab.", Biochem. & Biophys Res Comm. vol. 46, No. 2 1972, pp. 738–744.

Nishikawa, et al., Competitive Nephlometric Immunoassay Method for Antiepilectic Drugs in Patient Blood, Journal of Immunological Method, 29 (1979) pp. 85–89.

*Primary Examiner*—Mary E. Ceperley
*Attorney, Agent, or Firm*—Raymond R. Wittekind

[57] ABSTRACT

Divalent hapten derivatives wherein two hapten moieties are connected by means of a bifunctional spacer wherein the derivative has the formula $$A-X-A$$

where A is a bonded hapten moiety and X is a bifunctional spacer having the formula $$(B)_m-Y-(CH_2)_n-Z-(CH_2)_n-Y-(B)_m$$

where m is independently 0 or 1, B is $(CH_2)_{n'}$, wherein n' is an integer from 1 to 4, or $CO(CH_2)_{n''}$, wherein n'' is an integer from 2 or 4; Y is independently —CONH—, —NHCO—, —OOC, —COO—, —O—, —S—, or —NR—, wherein R is hydrogen or alkyl; n is an integer from 1 to 10; and Z is an organic moiety containing at least one hydrophilic atom, useful for the determination of haptens by immunochemical techniques are disclosed.

10 Claims, No Drawings

DIVALENT HAPTEN DERIVATIVES

This is a division of application Ser. No. 07/069,747, now U.S. Pat. No. 4,760,142 granted Jul. 26, 1988, filed Jul. 6, 1987, which is a continuation-in-part of application Ser. No. 06/825,425 filed Feb. 3, 1986, now abandoned, which is a continuation-in-part of application Ser. No. 06/675,374 filed Nov. 27, 1984, now abandoned.

BACKGROUND OF THE INVENTION

A hapten may be defined as a chemical composition of limited molecular weight (usually less than 1000) which in and of itself does not elicit antibody formation when introduced into a host animal. However, when covalently bonded to a high molecular weight antigenic carrier, the resultant hapten-carrier conjugate can elicit in the host animal the formation of antibodies which recognize the hapten composition. Examples of haptens to which antibodies have been raised in this fashion are numerous, including such classes of materials as medicaments (therapeutic drugs), amino acids and metabolites, small peptides, steroids and aromatic residues such as the dinitrophenyl moiety. Typical carriers are large polyvalent molecules such as proteins, polysaccharides and glycoproteins which are not native to the host animal. The methods for preparation of hapten-carrier conjugates are well known in the art and have been reviewed (B. F. Erlanger; *Methods in Enzymology*, v. 70, p. 84, 1980).

A divalent hapten may be considered as a subclass of hapten-carrier conjugates. The carrier, which may be of any molecular weight, is covalently bonded to the haptens by means of only two functional groups. The two functions may be different but they are generally the same. The carrier molecule also may be of any molecular weight or of any molecular shape.

The carriers disclosed herein function primarily to separate the two hapten moieties by a chemical spacer. Because of their divalent character they can bridge antigen binding sites on adjacent antibody molecules directed towards hapten, thus differentiating them from free hapten.

The concept of divalent haptens for bridging adjacent antibody molecules was investigated by R. C. Valentine and N. M. Green for a series of 2,4-dinitrophenylated polymethylenediamines (J. Molecular Biol., 27, 615 1967). It was found that a minimum of an eight carbon length spacer allowed bridging of antibodies. However, the water solubility of the spacers described by Valentine and Green was found to be very poor. A divalent hapten system which is more water soluble is needed and desired.

In recent times, particular interest has been directed at a clinical assay method of diagnosis in which the pathological state or the pathological prognosis of a patient is assessed, or the medicament dose which is to be administered to the patient is determined, in such a manner that the content in the urine or blood of a physiologically active substance which has a low molecular weight and is in this body in the form of a hapten (and its metabolites), or of a medicament (and its metabolites) which has been administered to the patient, is measured.

Examples of the haptens to be measured in carrying out this clinical assay method or diagnosis include thyroid hormones such as, for example, L-3,3'5-tri-iodothyronine ($T_3$) and L-thyroxine ($T_4$).

The medicaments which are to be measured in this assay method or diagnosis include medicaments whose dose should be determined with extreme care and whose actions exhibit a relation to their concentration in the blood or urine. Some typical medicaments include digitalis preparations, antibiotics such as tetracycline, psychotropic agents such as amphetamine, narcotics such as morphine, blood coagulants and anticoagulants, and in particular theophylline and phenobarbital.

The haptens are usually found in trace quantities, being present in blood or urine as complex-bound or conjugated forms with complicated compositions. For this reason, an elaborate and time-consuming method to determine and measure them is required.

A variety of methods can be used to measure these haptens, namely physicochemical methods, immunochemical methods or competitive protein-binding methods.

Immunochemical methods are now considered superior to physicochemical methods due to the reaction specificity and sensitivity of measurement. A large number of immunochemical methods for the measurement of traces of haptens in the human body are known at present, for example agglutination inhibition methods, radioimmunoassay (RIA) and enzyme immunoassay (EIA). In a known EIA method, use is made of particles which are loaded with the antibody to the hapten which is to be measured and of a coupling product of the hapten with a carrier substance (See, German Offenlegungsschrift 2,155,658 and German Patent 2,743,445).

The procedure for an agglutination inhibition method entails the use of a coupling product of a hapten, which is the same hapten as the hapten which is to be measured, and a carrier substance, such as a protein, a polysaccharide or a glycoprotein, bound to solid particles, for example blood cells or latex with a high molecular weight, as the antigen. An antibody to the hapten which is to be measured is obtained from an antiserum which is obtained from mammals, for example guinea pigs, rabbits or sheep, which have been immunized with the coupling product of the hapten and the carrier substance.

When the antibody is mixed with the fine particles onto which the hapten-carrier conjugates are coupled an agglutination reaction between these two components takes place. The agglutination reaction is inhibited when the hapten which is to be measured is present in the sample. This method is an extremely straightforward method which is able to measure the hapten which is present in the blood or urine in the form of a complex or conjugate, without the necessity for complicated methodological measures, Such as hydrolysis or chromatography. The sensitivity of this method is about 100 ng/ml, even if blood cells are used as the particles. However, since most haptens which are of interest to measure in the human body are present in quantities between 500 pg/ml and 50 ng/ml, they must be concentrated in order to carry out successful measurement.

It is desired to develop a new immunochemical method for the measurement of haptens by inhibition of agglutination which exhibits higher sensitivity of measurement than the heretofore known methods.

SUMMARY OF THE INVENTION

This invention relates to a divalent hapten derivative. More particularly, this invention relates to a derivative wherein two hapten moieties are connected by means of a bifunctional spacer wherein the derivative has the formula

A—X—A where A is a bonded hapten moiety and X is a bifunctional spacer having the formula $(B)_m-Y-(CH_2)_n-Z-(CH_2)_n-Y-(B)_m$ where m is independently 0 or 1, B is $(CH_2)_{n'}$, wherein n' is an integer from 1 to 4, or $CO(CH_2)_{n''}$, wherein n" is an integer from 2 to 4; Y is independently —CONH—, —NHCO—, —OOC—, —COO—, —O—, —S—, or —NR—, wherein R is hydrogen or alkyl; n is an integer from 1 to 10; and Z is an organic moiety containing at least one hydrophilic atom.

DETAILED DESCRIPTION OF THE INVENTION

This invention relates to a divalent hapten derivative in which two hapten moieties are coupled by means of a bifunctional spacer having the formula

A—X—A where A is a bonded hapten moiety and X is a bifunctional spacer having the formula $(B)_m-Y-(CH_2)_n-Z-(CH_2)_n-Y-(B)_m$ where m is independently 0 or 1; B is $(CH_2)_{n'}$, wherein n' is an integer from 1 to 4, or wherein n" is an integer from 2 to 4; Y is independently —CONH—, —NH-CO—, —OOC—, —COO—, —O—, —S— or —NR—, wherein R is hydrogen or alkyl; n is an integer from 1 to 10; and Z is an organic: moiety containing at least one hydrophilic atom.

Unless otherwise stated, the following definitions shall apply throughout the specification and the appended claims.

The term "alkyl" shall mean a straight or branched chain saturated hydrocarbon group having 1 to 6 carbon atoms, e.g. methyl, ethyl, isopropyl, 2-butyl, neopentyl, n-hexyl, etc; the term "alkylene" refers to a bivalent radical of the branched or unbranched alkyl group it is derived from having valence bonds from two terminal carbons thereof, e.g. ethylene (—CH$_2$CH$_2$), propylene (—CH$_2$CHCH$_2$—), isopropylene (CH$_3$CH—CH$_2$—), etc.; the term "hydrophilic atom" is defined as an atom which is capable of forming a hydrogen bond with water, formation of which aids in the dissolution of the associated divalent hapten A in aqueous media. Examples of hydrophilic atoms which are capable of forming strong hydrogen bonds with water are oxygen and nitrogen. Suitable Z groups containing these atoms are: ethers of the formula -alkylene-O-alkylene-; secondary amines of the formula -alkylene-NH-alkylene-; tertiary amines of the formula -alkylene-N-alkylene-;
      |
      alkyl secondary alcohols of the formula OH
          |
-alkylene-CH-alkylene-;

tertiary alcohols of the formula

OH
          |
-alkylene-C-alkylene-;
          |
          alkyl sulfones of the formula

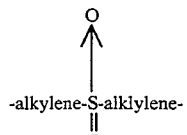

and sulfoxides of the formula

Particularly preferred Z moieties are those containing two hydrophilic atoms such as, bis-ethers of the formula -O-alkylene-O-; bis-secondary amines of the formula —NH—alkylene—NH—; and bis-tertiary amines of the formula

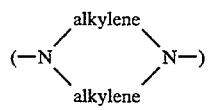

The invention disclosed herein is a new class of divalent haptens in which the carrier (herein simply referred to as bifunctional spacer) is a homobifunctional, predominately linear organic molecule in which one or more heteroatoms have been substituted for carbon atoms. Examples of preferred heteroatoms are oxygen and nitrogen. Incorporation of these heteroatoms imparts a significant increase in water solubility to the hapten conjugates over analogs in which they are absent. For hydrophobic haptens, this solubilizing feature of the spacer allows the constitution of the divalent haptens in aqueous buffers suitable for subsequent interaction with antibodies.

Haptens may be coupled to the bifunctional spacer by a variety of covalent bonds, but a particularly preferred method is formation of an amide bond, For the formation of an amide bond, the hapten must either contain a carboxyl function or be readily converted thereto. An example of a suitable hapten which contains a carboxyl function is L-thyroxine. Examples of haptens to which a carboxyl group may be introduced include theophylline, phenytoin and phenobarbital.

In those cases where the hapten to be coupled does not contain a carboxyl function, it may be introduced by a variety of methods known to those skilled in the art. For instance, those haptens which contain a nucleophilic function such as amine, alcohol or thiol may be alkylated with a halo-alkyl-carboxylic acid or reacted with succinic anhydride to give a hemisuccinate.

If amine functions or other reactive groups are present in the hapten, such as in the case of amino acids, these must be masked by a protecting group before attempting condensation with the diamine bifunctional spacer. Protecting groups may be chosen from any of those well known in the art as long as their subsequent removal after conjugation does not interfere with the integrity of the divalent hapten. Suitable protecting groups include t-butyloxycarbonyl, benzyloxycarbonyl and trifluoroacetyl, and suitable masking procedures are well known in the art.

The bifunctional spacer of this invention is chosen to have a length such that steric interactions between immobilized antibody particles are minimized. In addition, the bifunctional spacer is chosen to contain features which lend water solubility to the divalent conjugate, for example by inclusion of hydrophilic atoms, such as nitrogen or oxygen. For this reason, component Z of the bifunctional spacer is chosen to be a group having at least one hydrophilic group such as for example, $-O-(CH_2)_4-O-$,

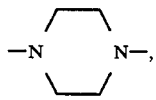

or $-NH-(CH_2)_4-NH-$, which provides water solubility to the conjugate. This feature provides an advantage of the instant compositions over those known in the art (See, J. Mol. Biol., 27, 615, 1967). Although it is not necessary for the practice of this invention that the bifunctional spacer be symmetrical in composition, it is preferred for convenience of synthesis.

Particularly preferred intermediates in the synthesis of bifunctional spacers are diamines of the following type $$NH_2-(CH_2)_n-Z-(CH_2)_n-NH_2$$

where Z is a bis-ether, bis-secondary amine, or bis-tertiary amine as defined above. In the practice of this invention, commercially available diamines are chosen. However, these can also be synthesized by methods well known in the art. For example, the diamine, where Z is a bis-ether are obtained by reacting a nitrilo-alkyl-bromide of the formula $NC-(CH_2)_{n-1}Br$ (I), with a glycol of the formula HO-alkylene-OH (II) in a dipolar aprotic solvent such as N,N-dimethylformamide or dimethylsulfoxide, at a temperature of 0° to 100° C. for 1 to 24 hours in the presence of suitable tertiary amine base e.g. triethylamine, tributylamine, etc. to give a bis-nitrilo intermediate of the formula III.

$$NC-(CH_2)_{n-1}-O-alkylene-O-(CH_2)_{n-1}CN \qquad (III)$$

Intermediate III is then subsequently reduced by catalytic hydrogenation, typically at 20° to 50° C. for 1 to 24 hours at a pressure of 10 to 50 psi in the presence of a suitable catalyst, such as for example, palladium on charcoal to give the desired diamine $$H_2N-(CH_2)_n-O-alkylene-O-(CH_2)_n-NH_2 \qquad (IV).$$

Similarly, the diamines where Z is a bis-amine are typically obtained by reacting nitrilo-alkyl-bromide I with a diamine of the formula

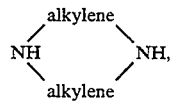

to give an intermediate of the formula

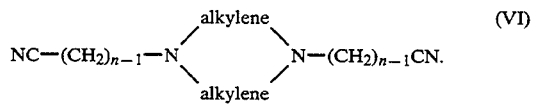

Typically this reaction is carried out in a dipolar aprotic solvent, such as for example, N,N-dimethylformamide, dimethylsulfoxide etc., at a temperature of 0° to 100° C. for 1 to 24 hours. Intermediate VI is then reduced catalytically, as described above, to yield the desired amine VII of the formula

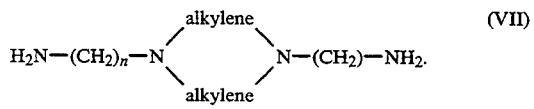

This coupling of the hapten carboxylate to a diamine bifunctional spacer is performed by preactivation of the carboxylic acid group by any of number of techniques well known in the art for amide bond formation. These include the use of condensing reagents such as carbodiimides or carbonyldiimidazole, as well as pre-formed anhydrides, acid chlorides, or active esters of the carboxylic acid. An unusual activated carboxyl function which is uniquely useful for theophylline is the cyclic lactam of the 8-butyric acid derivative (See example 5 herein).

The coupling of the activated hapten carboxylate to the diamine bifunctional spacer is performed with a minimum molar ratio of 2 haptens per bifunctional spacer, and preferably with a moderate excess of hapten moiety in order to drive the reaction to completion. Coupling may be employed in a variety of solvents. Particularly preferred solvents are those of the dipolar aprotic type, such as dimethylformamide or dimethylsulfoxide.

The final reaction mixture generally is composed exclusively of divalent hapten conjugate and excess activated hapten carboxylate. Isolation of the divalent hapten is generally accomplished by selective precipitation or crystallization. In more difficult cases, chromatographic methods such as silica gel chromatography may be used to advantage.

The divalent hapten derivatives of this invention may be used in turbidimetric drug assays. It is anticipated that this can be accomplished by removing a particular volume of the body fluid or of the excretion which contain the hapten which is to be measured and using it directly as the sample solution or diluting it appropriately to various concentrations, whereupon the reaction between a specified volume of the assay solution and a specified volume of a suspension of particles loaded with the antibody is allowed to take place. Thereafter, a specified volume of the divalent hapten is added to this reaction mixture to form the extended complex. After a particular reaction time, a nephelometric or turbidimetric measurement is carried out. The evaluation makes use of a reference curve measured in parallel.

For example, the divalent hapten derivatives of the invention may be used in a method for conducting a turbidimetric assay comprising a) obtaining an antibody to the hapten to be assayed;
b) immobilizing said antibody on a macromolecular carrier to form an immobilized antibody;
c) incubating said immobilized antibody with a divalent hapten derivative comprising two hapten moieties connected by means of a bifunctional spacer having the formula

A—X—A where A is a bonded hapten moiety and X is a bifunctional spacer having the formula $(B)_m$—Y—$(CH_2)_n$—Z—$(CH_2)_n$—Y—$(B)_m$ where m is independently 0 or 1, B is $(CH_2)_{n'}$, wherein n' is an integer from 1 to 4, or $CO(CH_2)_{n''}$, wherein n" is an integer from 2-4; Y is independently —CONH—, —NHCO—, —OOC—, —COO—, —O—, —S—, or —NR—, wherein R is hydrogen or alkyl; n is an integer from 1 to 10; and Z is an organic residue having at least one hydrophilic atom;

d) measuring the turbidity of said extended complex;
e) incubating said measured extended complex with the sample to be assayed to form the assay solution;
f) measuring the turbidity of said assay solution;
g) comparing the measurement obtained from measuring the turbidity of said extended complex with the measurement obtained from measuring the turbidity of said assay solution to obtain a comparison; and
h) calculating the amount of the hapten to be assayed which is present in said sample.

The antibodies to the hapten are obtained in a known manner, as follows: a hapten is coupled to a carrier substance. An antiserum is obtained from an animal which has been immunized by a routine method with the hapten coupled to the carrier as the antigen. The antibodies to the hapten are obtained in such a manner that the other antibodies, i.e., the antibodies to the carrier and/or the part of the molecule between the carrier and the hapten, are removed by absorption. Any desired materials can be used as carrier substances. Good results are obtained when the carrer substances have high antigenicity. Suitable substances include Keyhole Limpet hemocyanin.

The particles which are to be loaded are finely divided carriers such as are normally used for carrying out immunochemical agglutination reactions or agglutination inhibition reactions, such as high molecular weight latex.

To load the latex particles, the antibody to the hapten, which has been obtained by the methods described above, is covalently bonded, such as in accordance with European Patent Application No. 82,110,273.8.

The hapten which is coupled to the carrier and is used to elicit an antibody to the hapten, and the divalent hapten used as a developer in the method of measurement, can differ from one another at the point of coupling between the carrier substance and the hapten.

Examples of haptens which are to be measured according to the invention are the medicaments theophylline, phenobarbital, diphenylhydantoin, digitoxin, primidone, valproic acid, carbamazepine, gentamycin, tobramycin and kanamycin.

Examples of other haptens to be measured according to the invention are thyroid hormones such as $T_3$ end $T_4$.

Compared with the conventional method, the invention provides extremely high sensitivity of measurement. Although its mechanism is not as yet completely explained, this high sensitivity is assumed to derive from the fact that the hapten antibody which has been loaded onto the particle acts as a multivalent binder.

Only small quantities of the antibody to the hapten and the divalent hapten are necessary according to the invention. Thus, these substances can be employed economically. For example, the quantity used of a particular divalent hapten, namely one comprising theophylline, can be reduced to about 1/100 to 1/1,000 of the quantity necessary to carry out the conventional method.

According to the conventional method, as described in German Patent 2,743,445, for the measurement of haptens by inhibition of agglutination, a hapten coupled to a carrier is used. As described in this patent, the sensitivity of measurement can be increased further if the hapten-carrier conjugate is bound to fine particles. We have found, surprisingly, that a divalent hapten derivative is more suitable for nephelometric measurement than is a hapten-protein carrier conjugate.

The advantage of the divalent hapten derivative are that the measurement is more sensitive and can be carried out in a shorter measuring time. Another great advantage is that the elaborate synthesis of a hapten-protein carrier conjugate, such as, for example, a hapten-apoferritin or hapten-albumin conjugate, is dispensed with. As is familiar to those skilled in the art, the protein-hapten conjugates mentioned can be prepared only with moderate yields, because of side reactions, and there are wide variations between batches. These derivatives are very heterogeneous in respect of molecular weight (protein-protein crosslinking) and the quantity of hapten loaded. The preparation of the divalent hapten derivatives is straightforward and the costs are favorable. Since no uncontrolled side reactions can occur, constancy between batches is ensured and can reliably be checked by means of analytical data (mass spectroscopic analysis, elemental analysis, infrared and nuclear magnetic resonance spectra).

The following examples are illustrative of the invention but it is understood that the invention is not limited thereto.

EXAMPLE 1

Theophylline-8-butyric acid 25 g of diaminodimethyluracil hydrate and 50 g of glutaric anhydride were refluxed in 250 ml dimethylaniline for 3 hours. The mixture was cooled and added to 1.5 liters of water and 50 ml of concentrated sodium hydroxide solution. The resulant solution was extracted with 300 ml of ether to remove dimethylaniline. The aqueous layer was diluted further with 1.5 liters of water, then passed through a 1.5 liters bed of Dowex 2 anion exchange resin in the formate form. The bed was washed with 6 liters of water, then 4 liters of 0.1M formic acid. The product was eluted with 0.2M formic acid in a 1:1 mixture of water and acetone. The eluates containing product were pooled and evaporated under reduced pressure to a crystalline slurry. The crystals were collected, washed with cold water, and recrystallized from hot isopropanol to give 20 g of theophylline-8-butyric acid.

EXAMPLE 2 bis-(Theophylline-8-butyryl)-1,6-hexanediamine

Theophylline-8-butyric acid, 1.0 g, was dissolved in 10 ml of dimethylformamide. Tributylamine, 0.89 ml, was added and the solution was chilled to 5° C. Isobutylchloroformate, 0.48 ml, was then added and the mixture was stirred for 10 minutes. Hexanediamine, 0.20 g, dissolved in 10 ml of dimethylformamide and chilled to 5° C. was then added. The reaction mixture was stirred for 30 minutes at 0°-5° C. A heavy gelatinous precipitate formed which was filtered off and washed with dimethylformamide. The product was dried in vacuum to yield 0.75 g of bis-(theophylline-8-butyryl)-1,6-hexanediamide.

EXAMPLE 3 bis-(Theophylline-8-butyryl)-4,9-dioxa-1,12-dodecane-diamide

The synthesis was performed as in example 2, substituting 0.40 ml of 4,9-dioxa-1,12-dodecanediamine for 1,6-hexanediamine. The reaction mixture, a solution, was poured into 500 ml of ethyl ether while stirring. After refrigeration overnight (about 16 hours), the suspension was filtered. The crude solid was recrystallized from methanol to give 0.45 g of bis-(theophylline-8-butyryl)-4,9-dioxa-1,12-dodecane-diamide.

EXAMPLE 4

Solubility comparison for bis-(theophylline-8-butyryl)-diamides

The bis-(theophylline-8-butyryl)-diamides of 1,6-hexanediamine and 4,9-dioxa-1,12-dodecanediamine (examples 2 and 3) were each dissolved in dimethylsulfoxide. The 4,9-dioxa-1,12-dodecanediamide dissolved readily to give a solution of 10 mg/0.5 ml at room temperature. This solution when diluted into 2 ml of 50 mM aqueous sodium phosphate buffer (pH 7.5) gave a clear, stable solution. On the other hand, the 1,6-hexanediamide required heating to obtain a solution of 10 mg/2 ml in dimethylsulfoxide and upon dilution of this solution into a two-fold volume of pH 7.5 phosphate buffer, immediate heavy precipitation of divalent hapten was noted.

EXAMPLE 5

Theophylline-8-butyric acid lactam

Theophylline-8-butyric acid, 24 g (example 1), was dissolved in 500 ml of acetic anhydride with heating. The mixture was gently refluxed for 30 minutes, then filtered through a preheated funnel to remove insoluble material. The product crystallized upon cooling. The product was collected, washed with ether and hexane then dried in vacuum at 50° C. to give 20 g of theophylline-8-butyric acid lactam.

EXAMPLE 5A bis-(Theophylline-8-butyryl)-N,N-bis-3-aminopropyl piperazine diamide Theophylline-8-butyric acid lactam (example 5), 0.5 g, was suspended in 5 ml dimethylformamide. Bis-(3-aminopropyl)piperazine, 0.2 ml, and tributylamine, 0.48 ml, were added with stirring. A solution was initially obtained but after 15 minutes, a heavy gelatinous precipitate formed. The reaction mixture was diluted with 5 ml dimethylformamide and stirred overnight. The precipitate was filtered off and washed with dimethylformamide. Drying gave 0.6 g of bis-(theophylline-8-butyryl)-N,N-bis-3-aminopropyl piperazine.

EXAMPLE 6

Phenobarbital-N-propionic acid

Phenobarbital, 93 g, and 3-bromopropionic acid, 74 g, were added to 200 ml of water. With mixing, 48 g of sodium hydroxide was then added. The mixture was heated on a steam bath with occasional swirling for 1.5 hours. At this time, an additional 16 g of sodium hydroxide was added and heating was continued for another 1.5 hours. The solution was diluted to 1.6 liters with water then adjusted to pH 6.5 with concentrated hydrochloric acid. A precipitate of unreacted phenobarbital formed. The mixture was extracted with ethyl acetate, 400 ml, three times to remove most of the phenobarbital. The remaining aqueous solution was adjusted to pH 4.5 with concentrated hydrochloric acid to give a milky suspension. The suspension was extracted twice with 400 ml ethyl acetate. The combined extract containing product was washed with water followed by saturated sodium chloride solution. The extract was dried over magnesium sulfate, filtered and evaporated to an oil. The oil was crystallized by dissolving in acetone and adding hexane to turbidity. The product was collected and dried to yield 20 g of phenobarbital-N-propionic acid.

EXAMPLE 7 bis-(Phenobarbital-N-propionyl)-4,9-dioxa-1,12-dodecanediamide

Phenobarbital-N-propionic acid, 1.27 g, was dissolved in 5 ml dimethylformamide. While stirring at room temperature, 0.61 g of carbonyldiimidazole dissolved in 5 ml of dimethylformamide was added dropwise. After 30 minutes, 0.40 ml of 4,9-dioxa-1,12-dodecanediamine in 5 ml of dimethylformamide was added dropwise. After addition was complete, the reaction was stirred at room temperature for 2 hours. The solvent was evaporated on high vacuum and the residue triturated with hexane to give a solid. The resultant crude product was dissolved in chloroform/methanol (9:1), 10 ml, and applied to a column of silica gel. The column was eluted with chloroform followed by chloroform/methanol mixtures ranging from 9:1 to 5:5. The product which eluted with 9:1 mixture was homogeneous by thin layer chromatography (TLC). The fractions were pooled and evaporated to an oil. Vacuum drying gave an amorphous solid, 0.65 g, of bis-(phenobarbital-N-propionyl)-4,9-dioxa-1,2-dodecanediamide.

EXAMPLE 8

Trifluoroacetyl-L-thyroxine

L-thyroxine, sodium salt, 10 g, was added with stirring to a chilled mixture of 150 ml ethyl acetate and 40 ml trifluoroacetic acid. To the resultant solution, 10 ml of trifluoroacetic anhydride was added dropwise. After addition was complete, the reaction was stirred for 2 hours at 0°-2° C. The reaction mixture was then poured into 200 ml ice-cold sodium chloride solution. The mixture was diluted with 100 ml ethyl acetate and the phases were separated. The ethyl acetate phase was washed with 1M sodium bisulfate followed by saturated sodium chloride solution. The solution was then dried over magnesium sulfate, filtered and concentrated to a small volume. Dilution with ether followed by low boiling petroleum ether gave a flocculent precipitate. The precipitate was collected and dried to give 8.2 g of product. Thin layer chromotography (TLC) showed a minor second spot for thyroxine. Purification by silica gel chromatography in chloroform/methanol (90:10) gave 4.3 g of trifluoroacetyl-L-thyroxine.

EXAMPLE 8A bis-(Trifluoroacetyl-L-thyroxyl)-4,9-dioxa-1,12-dodecanediamide

Trifluoroacetyl-L-thyroxine (example 8), 1.23 g, was dissolved in 8 ml tetrahydrofuran and the solution was chilled to −2° C. in an ice/acetone bath. N-methylmorpholine, 0.16 ml, was added followed by isobutylchloroformate, 0.18 ml. After stirring for 7 minutes, a solution of 0.15 ml 4,9-dioxa-1,12-dodecanediamine in 2 ml tetrahydrofuran was added dropwise over 5 minutes. The mixture was stirred at 0° C. for 30 minutes then warmed up to room temperature. The reaction was filtered to remove salts and the filtrate evaporated to an oil. The oil was redissolved in ethyl acetate and the solution was washed with aqueous 1M sodium bisulfate followed by 0.5M sodium chloride. The ethyl acetate solution was dried over magnesium sulfate, filtered and concentrated to an oil. The oil was crystallized from ethyl acetate/hexane to obtain 0.6 g of bis-(trifluoroacetyl-L-thyroxyl)-4,9-dioxa-1,12-dodecanediamide from two crops.

EXAMPLE 9 bis-(L-thyroxyl)-4,9-dioxa-1,12-dodecanediamide, dihydrochloride salt

Bis-(trifluoroacetyl-L-thyroxyl)-4,9-dioxadodecane-1,12-diamide (example 8A), 0.34 g, was dissolved in 3 ml methanol. 1M sodium hydroxide was added with stirring and the reaction was allowed to go at room temperature for 40 hours. The reaction mixture was diluted into 20 ml of cold 1M hydrochloric acid to give a fine suspension of product. The suspension was centrifuged and the pellet was dissolved in ethanol. The ethanol solution was evaporated to a solid residue of crude product. The product was recrystallized from methanol/ether to obtain 0.18 g of bis-(L-thyroxyl)-4,9-dioxa-1,12-dodecanediamide, dihydrochloride salt.

EXAMPLE 10

Bis-(N-succinyl-L-thyroxyl)-4,9-dioxa-1,12-dodecanediamide

A solution of 2.0 g succinic anhydride in 20 ml pyridine was added dropwise to a chilled solution of 2.0 g 4,9-dioxa-1,12-dodecanediamine in 20 ml pyridine. The reaction mixture was stored at 4° C. for 18 hours then evaporated to a solid residue. The residue was dissolved in 30 ml water and passed through a bed of 30 ml Dowex 50 cation-exchange resin in the $H^+$ form. The bed was then washed with 60 ml water. The effluent was concentrated to about half-volume to give colorless crystals of bis-succinyl-4,9-dioxa-1,12-dodecanediamide which were collected and dried. The yield was 2.18 g.

The intermediate was dissolved in 30 ml of dimethylformamide along with 1.5 g N-hydroxysuccinimide. The solution was chilled and 2.45 g dicyclohexyl-carbodiimide in 15 ml dimethylformamide was added all at once. After 18 hours at 4° C., the reaction mixture was filtered and the filtrate evaporated to an oil. The oil was crystallized from isopropanol and ether to give a crystalline product of 1.3 g bis-succinimido O,N-succinyl-4,9-dioxa-1,12-dodecanediamide. The latter active ester, 0.3 g, was dissolved in 2 ml dimethylformamide and added dropwise to a suspension of 0.89 g L-thyroxine, sodium salt in 4 ml dimethylformamide containing 0.11 ml N-methylmorpholine. The reaction mixture was stirred for 72 hours. The resultant solution was evaporated to an oil. The oil was washed with a mixture of ethyl acetate and 1M sodium bisulfate to give a solid which was collected by filtration, washed with water then methanol and dried to give 0.22 g of bis-(N-succinyl-L-thyroxyl)-4,9-dioxa-1,12-dodecanediamide.

The following examples are illustrative of turbidimetric analysis according to this invention using the divalent hapten derivative of this invention.

EXAMPLE 11

The divalent hapten used is bis-(theophylline-8-butyryl)-N,N'-bis-3-aminopropyl-piperazine diamide.

The divalent hapten was dissolved in dimethyl sulfoxide at a concentration of 1 mg/ml, and then diluted 1:51,200 in distilled water, with the addition of 4% human serum albumin. The diluted divalent hapten acts as a "developer" in the assay. A latex reagent was prepared by binding antiserum to theophylline onto polystyrene latex. The anti-theophylline latex reagent was prepared as described in European Patent 82,110,273.8. For the measurement, 10 ul of a sample containing theophylline, diluted 1:100 in a 0.1M glycine/NaCl buffer, pH 8.0, was mixed in a cuvette with 10 ul of the developer dilution described above and with 20 ul of a phosphate-buffered sodium chloride solution containing 4.6% of polyethylene glycol 6000 and with 10 ul of the antitheophylline latex reagent described above. The mixture was incubated at room temperature for 12 minutes. Then, a further 200 ul of a phosphate-buffered sodium chloride solution containing 4.6% of polyethylene glycol 6000 was added, mixed in, and the light scattering measured in a commercially available laser nephelometer (Behring laser nephelometer).

An incubation curve was Obtained with different quantities of theophylline added. The measuring range extended from about 1 to 40 ug/ml theophylline.

EXAMPLE 11A

For comparison, a conventional measurement with an apoferritin developer was carried out. The apoferritin-theophylline derivative is commercially available (Kallestad batch Number: R1). It was diluted 1:1,280 in aqueous human serum albumin solution and used in this dilution as the developer in the assay. The mixture for the measurement was made up as described previously, with the single exception that the apoferritin-theophylline derivative was used in place of the divalent hapten developer. The inhibition curve in this case obtained with different quantities of theophylline added showed lower sensitivity, i.e., the lower detection limit is higher.

EXAMPLE 12

The divalent hapten used is bis-(phenobarbital-N-propionyl)-4,9-dioxa-1,12-dodecanediamide.

The divalent hapten was dissolved in dimethyl sulfoxide at a concentration of 1 mg/ml and then diluted 1:40,000 in aqueous 4% strength human serum albumin solution. The diluted divalent hapten acts as a "developer" in the assay.

A latex reagent was prepared by binding antiserum to phenobarbital onto polystyrene latex. The anti-phenobarbital latex reagent was prepared as described in European Patent 82,110,273.8.

For the measurement, 20 ul of a sample containing phenobarbital, diluted 1:100 in 0.1M glycine/NaCl buffer, pH 8.0, was mixed in a cuvette with 20 ul of the developer dilution described above with 40 ul of a phosphate-buffered sodium chloride solution containing 4.6% of polyethylene glycol 6000 and with 20 ul of the anti-phenobarbital latex reagent described above. The mixture was incubated at room temperature for 25 minutes. A further 200 ul of a phosphate-buffered sodium chloride solution containing 4.6% of polyethylene glycol 6000 was then added, mixed in and the light scattering measured in a commercially available laser nephelometer (Behring laser nephelometer). An incubation curve is obtained with different quantities of phenobarbital added. The measurement range extended from about 2.5 to 80 ug/ml phenobarbital.

EXAMPLE 12A

For comparison, a conventional measurement with an apoferritin developer was carried out. The apoferritin-phenobarbital derivative is commercially available (Kallestad batch Number 026-S1). It was diluted 1:750 in aqueous human serum albumin solution and used in this dilution as the developer in the assay. The mixture for the measurement was made up as described previously, with the apoferritin-phenobarbital derivative being employed in place of the divalent hapten developer. A very flat incubation curve in this case resulted with different quantites of phenobarbital added, and thus it was determined that this can not be used for satisfactorily reproducible measurement.

We claim:

1. A method for conducting a turbidimetric assay comprising:
   a) obtaining an antibody to the hapten to be assayed;
   b) immobilizing said antibody on a macromolecular carrier to form an immobilized antibody;
   c) incubating said immobilized antibody with a divalent hapten derivative comprising two hapten moieties connected by means of bifunctional spacer having the formula

A—X—A wherein A is a hapten moiety and X is a bifunctional spacer having the formula $(B)_m$—Y—$(CH_2)_n$—Z—$(CH_2)_n$—Y—$(B)_m$ wherein m is independently 0 or 1, B is $(CH_2)_{n'}$, wherein n' is an integer from 1 to 4, or $CO(CH_2)_{n''}$, wherein n'' is an integer from 2–4; Y is independently —CONH—, —NHCO—, —OOC—, —COO—, —O—, —S—, or —NR—, wherein R is hydrogen or alkyl; n is an integer from 1 to 10; and Z is selected from the group consisting of -alkylene-O-alkylene-, alkylene-NH-alkylene, alkylene—N—alkylene,
   |
   alkyl —N(—alkylene—)N—, -continued
   —NH—alkylene—NH, —O—alkylene—O—alkylene—CH(OH)—alkylene, —alkylene—C(OH)(alkyl)—alkylene—, —O—alkylene—O—, —alkylene—S(=O)—alkylene—, and —alkylene—S(↓O)—alkylene—.

where the term alkyl means a straight or branched chain saturated hydrocarbon group having 1 to 6 carbon atoms and the term alkylene refers to a bivalent radical of the branched or unbranched alkyl group having valence bonds from two terminal carbons thereof to form an extended complex;
   d) measuring the turbidity of said extended complex;
   e) incubating said extended complex with the sample to be assayed to form the assay solution;
   f) measuring the turbidity of said assay solution;
   g) comparing the measurement obtained from measuring the turbidity of said extended complex with the measurement obtained from measuring the turbidity of said assay solution to obtain a comparison; and
   h) calculating the amount of the hapten to be assayed which is present in said sample.

2. The method of claim 1 wherein said component Z is selected from the group consisting of —O—$(CH_2)_4$—O—, —N(—piperazine—)N—, and —NH$(CH_2)_4$—NH—.

3. The method of claim 1 wherein said divalent hapten derivative comprises bis-(theophylline-8-butyryl)-4,9-dioxa-1,12-dodecanediamide.

4. The method of claim 1 wherein said divalent hapten derivative comprises bis-(theophylline-8-butyryl)-N,N-bis-3-aminopropylpiperazinediamide.

5. The method of claim 1 wherein said divalent hapten derivative comprises bis-(phenobarbital-N-propionyl)-4,9-dioxa-1,12-dodecanediamide.

6. The method of claim 1 wherein said divalent hapten derivative comprises bis-(trifluoroacetyl-L-thyroxyl)-4,9-dioxa-1,12-dodecanediamide.

7. The method of claim 1 wherein said divalent hapten derivative comprises bis-(L-thyroxyl)-4,9-dioxa-1,12-dodecanediamide, dihydrochloride salt.

8. The method of claim 1 wherein said divalent hapten derivative comprises bis-(N-succinyl-L-thyroxyl)-4,9-dioxa-1,12-dodecanediamide.

9. The method of claim 1 wherein said carrier is a latex particle.

10. The method of claim 1 wherein said turbidity is measured by laser nephelometry.

* * * * *